US007651525B2

(12) United States Patent
Dolan

(10) Patent No.: US 7,651,525 B2
(45) Date of Patent: Jan. 26, 2010

(54) INTRALUMINAL STENT ASSEMBLY AND METHOD OF DEPLOYING THE SAME

(75) Inventor: Mark J. Dolan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 935 days.

(21) Appl. No.: 10/911,931

(22) Filed: Aug. 5, 2004

(65) Prior Publication Data

US 2006/0030922 A1 Feb. 9, 2006

(51) Int. Cl.
*A61F 2/06* (2006.01)
(52) U.S. Cl. .................. 623/1.2; 623/1.11
(58) Field of Classification Search ........... 606/108, 606/191–198; 623/1.11, 1.12, 1.16
See application file for complete search history.

(56) References Cited

U.S. PATENT DOCUMENTS

| | | | |
|---|---|---|---|
| 4,464,176 A | 8/1984 | Wijayarathna | |
| 5,704,926 A | 1/1998 | Sutton | |
| 5,833,694 A | 11/1998 | Poncet | |
| 6,042,589 A * | 3/2000 | Marianne | 606/108 |
| 6,203,558 B1 * | 3/2001 | Dusbabek et al. | 606/198 |
| 6,245,076 B1 | 6/2001 | Yan | |
| 6,309,402 B1 | 10/2001 | Jendersee et al. | |
| 6,331,189 B1 | 12/2001 | Wolinsky et al. | |
| 6,375,676 B1 | 4/2002 | Cox | |
| 6,395,008 B1 | 5/2002 | Ellis et al. | |
| 6,458,138 B1 | 10/2002 | Sydney et al. | |
| 6,464,718 B1 * | 10/2002 | Miller et al. | 623/1.11 |
| 6,589,274 B2 | 7/2003 | Stiger et al. | |
| 6,613,079 B1 | 9/2003 | Wolinsky et al. | |
| 6,620,193 B1 | 9/2003 | Lau et al. | |
| 7,294,146 B2 * | 11/2007 | Chew et al. | 623/1.12 |
| 7,309,350 B2 * | 12/2007 | Landreville et al. | 623/1.11 |
| 2002/0099405 A1 | 7/2002 | Yurek et al. | |

FOREIGN PATENT DOCUMENTS

| | | |
|---|---|---|
| WO | WO 00/57815 | 10/2000 |
| WO | WO 01/17602 | 3/2001 |
| WO | WO 02/089705 | 11/2002 |

* cited by examiner

*Primary Examiner*—Kevin T Truong

(57) ABSTRACT

Intraluminal stent assemblies and methods of deploying the same. The assemblies include a catheter including at least one lumen formed therein. At least one inflatable member is disposed on the catheter and in communication with the lumen. The inflatable member includes at least one distal projection and/or at least one retention material. A stent is expandable from a compressed configuration to an expanded configuration. The stent is disposed on the inflatable member in the compressed configuration. A sheath is slidably positioned over the stent wherein the stent expands to the expanded configuration upon retraction of the sheath. The inflatable member is inflated with a fluid flowing through the lumen. The at least one distal projection and/or at least one retention material retain the stent in position on the inflatable member while the stent is being deployed.

21 Claims, 6 Drawing Sheets

INTRALUMINAL STENT ASSEMBLY AND METHOD OF DEPLOYING THE SAME

TECHNICAL FIELD OF THE INVENTION

The present invention relates generally to medical catheters. More particularly, the invention relates to an intraluminal stent assembly and method of deploying the same.

BACKGROUND OF THE INVENTION

Heart disease, specifically coronary artery disease, is a major cause of death, disability, and healthcare expense. A number of strategies have been developed for treating coronary heart disease, some of which are specifically designed to treat the complications resulting from atherosclerosis and other forms of coronary arterial narrowing.

An important development for treating atherosclerosis and other forms of coronary narrowing is percutaneous transluminal coronary angioplasty, hereinafter referred to as "angioplasty" or "PTCA". One objective in angioplasty is to enlarge the lumen of the affected coronary artery by radial hydraulic expansion. The procedure may be accomplished by inflating a balloon within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the blood vessel lumen. The wall of the artery itself may also be stretched when the balloon is inflated.

Angioplasty may be performed as follows: A thin walled hollow guiding catheter may be introduced into the body via a relatively large vessel, such as the femoral artery in the groin area or the brachial artery in the arm. Once access to the femoral artery is achieved, a short hollow sheath, or guiding catheter, may be inserted to maintain a passageway during the procedure. The flexible guiding catheter may negotiate an approximately 180 degree turn through the aortic arch to descend into the aortic cusp where entry is gained to either the left or the right coronary artery, as desired.

After the guiding catheter is advanced to the area to be treated by angioplasty, a flexible guidewire may be inserted into the guiding catheter through an expandable balloon and advanced to the area to be treated. The guidewire may be advanced beyond the lesion in preparation for the advancement of a balloon catheter having an expandable balloon portion composed of a resilient material. The balloon catheter may be advanced into position by sliding it along the guide wire. The use of the relatively rigid guide wire is desirable for steerability to advance the catheter through the narrowed lumen of the artery and to direct the balloon, which is typically quite flexible, across the lesion. Radiopaque markers in the balloon segment of the catheter facilitate positioning across the lesion. The balloon catheter may then be inflated with contrast material to permit fluoroscopic viewing during treatment. The balloon is alternately inflated and deflated until the lumen of the artery is satisfactorily enlarged.

While the affected artery generally may be enlarged, in some instances the vessel re-narrows (restenosis) acutely or chronically with time, thereby negating the positive effect of the angioplasty procedure. In the past, vessel restenosis has frequently necessitated repeat PTCA or open heart surgery. While vessel restenosis may not occur in the majority of cases, it occurs frequently enough that such complications comprise a significant percentage of the overall failures of the PTCA procedure, for example, twenty-five to thirty-five percent of such failures.

To lessen the risk of vessel restenosis, various devices have been developed for mechanically maintaining the patency of the affected vessel after completion of the angioplasty procedure. Such mechanical endoprosthetic devices, which are generally referred to as stents, are typically inserted into the vessel in a radially compressed configuration, positioned across the lesion, and then expanded into contact with the vessel wall to maintain an open passageway. Effectively, the stent overcomes the natural tendency of the vessel walls of some patients to re-narrow, thereby maintaining a more normal flow of blood through that vessel than would be possible if the stent were not in place. The stent is typically a cylindrically shaped device formed from wire(s) or a tube and intended to act as a permanent prosthesis. A typical stent may range from about 5 mm to 50 mm in length.

Various types of stents have been proposed, including expandable and self-expanding varieties. Expandable stents are generally conveyed to the area to be treated on balloon catheter assemblies or other expandable devices. For insertion, the stent may be positioned in a compressed configuration along the delivery device, such as a balloon catheter defining a balloon with two folded and wrapped wings, to minimize the stent diameter. After the stent is positioned across the lesion, the stent may be expanded by the delivery device, causing the length of the stent to contract and the diameter to expand. Depending on the materials used in construction of the stent, the stent maintains the new shape either through mechanical force or otherwise.

Self-expanding stents are generally conveyed to the area to be treated on catheter assemblies. Such stents are generally manufactured from resilient materials that can be compressed and then naturally re-expand when deployed. As such, self-expanding stents typically do not require a balloon to provide an expansion force. Some stent designs include a sheath placed over the compressed stent (and balloon assembly) to retain the stent on the balloon and to create an even outer surface on the assembly for negotiation through the narrowed vessels. The sheath may also be used to maintain a self-expanding stent in its compressed configuration. Once the catheter assembly is positioned, the stent may expand as the sheath is slidably retracted.

Prior art stents have included coiled stainless steel springs; helical wound spring coil made from shape memory alloy; expanding metal stents formed in a zig-zag pattern; diamond shaped, rectangular shaped, and other mesh and non-mesh designs. Exemplary stents and catheter assemblies including balloon mounted stents are disclosed in U.S. Pat. No. 6,613,079 issued to Wolinsky, et al.; U.S. Pat. No. 6,589,274 issued to Stiger, et al.; U.S. Pat. No. 6,331,189 issued to Wolinsky, et al.; U.S. Pat. No. 5,833,694 issued to Poncet; and U.S. Pat. No. 6,375,676 issued to Cox.

Some difficulties have been encountered with the deployment of certain self-expanding stents, including difficulties related to placement accuracy. For example, some self-expanding stents can store energy axially from the frictional force generated as the outer restraining sheath is retracted from the expanding stent. This may cause the stent to act somewhat like a spring, storing energy as the frictional force acts on the stent. As the stent expands beyond the end of the sheath, the stored energy may be immediately released, causing the stent to "jump" or slip. This may result in an inaccurate placement of the stent within the body vessel. As such, it would be desirable to provide a strategy for deploying a self-expanding stent that would limit jumping and slippage thereby increasing the accuracy of stent placement.

Accordingly, it would be desirable to provide an intraluminal stent assembly and method of deploying the same that would overcome the aforementioned and other disadvantages.

SUMMARY OF THE INVENTION

A first aspect according to the invention provides an intraluminal stent assembly. The assembly comprises a catheter including at least one lumen formed therein. At least one inflatable member is disposed on the catheter and in communication with the lumen. The inflatable member comprises at least one distal projection. A self-expanding stent is expandable from a compressed configuration to an expanded configuration. The stent is disposed on the inflatable member in the compressed configuration. A sheath is slidably positioned over the stent wherein the stent expands to the expanded configuration upon retraction of the sheath. The inflatable member is inflated with a fluid flowing through the lumen. The at least one distal projection retains the stent on the inflatable member while the stent is being deployed.

A second aspect according to the invention provides a method of deploying an intraluminal stent. The method comprises providing a self-expanding stent mounted on at least one inflatable member of an inflation catheter. The inflatable member comprises at least one distal projection. A sheath is positioned over the mounted stent. The mounted stent is positioned at a treatment site within a body lumen. The inflatable member is inflated and the sheath is retracted. The mounted stent self-expands and the stent is retained during its expansion with the distal projection. The inflatable member is then deflated and the inflation catheter is removed from the body lumen. The stent remains deployed at the treatment site in the body lumen.

A third aspect according to the invention provides an intraluminal stent assembly. The assembly comprises a self-expanding stent mounted on at least one inflatable member of an inflation catheter, sheath means, and retention means for retaining the stent on the inflatable member during stent deployment.

A fourth aspect according to the invention provides an intraluminal stent assembly. The assembly comprises a catheter including at least one lumen formed therein. At least one inflatable member is disposed on the catheter and in communication with the lumen. The inflatable member comprises at least one retention material. A self-expanding stent is expandable from a compressed configuration to an expanded configuration. The stent is disposed on the inflatable member in the compressed configuration. A sheath is slidably positioned over the stent wherein the stent expands to the expanded configuration upon retraction of the sheath. The inflatable member is inflated with a fluid flowing through the lumen. The at least one retention material retains the stent on the inflatable member while the stent is being deployed.

A fifth aspect according to the invention provides a method of deploying an intraluminal stent. The method comprises providing a self-expanding stent mounted on at least one inflatable member of an inflation catheter. The inflatable member comprises at least one retention material. A sheath is positioned over the mounted stent. The mounted stent is positioned at a treatment site within a body lumen. The inflatable member is inflated and the sheath is retracted. The mounted stent self-expands and the stent is retained during its expansion with the at least one retention material. The inflatable member is then deflated and the inflation catheter is removed from the body lumen. The stent remains deployed at the treatment site in the body lumen.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DESCRIPTION OF THE PRESENTLY PREFERRED EMBODIMENTS

Figure 1:
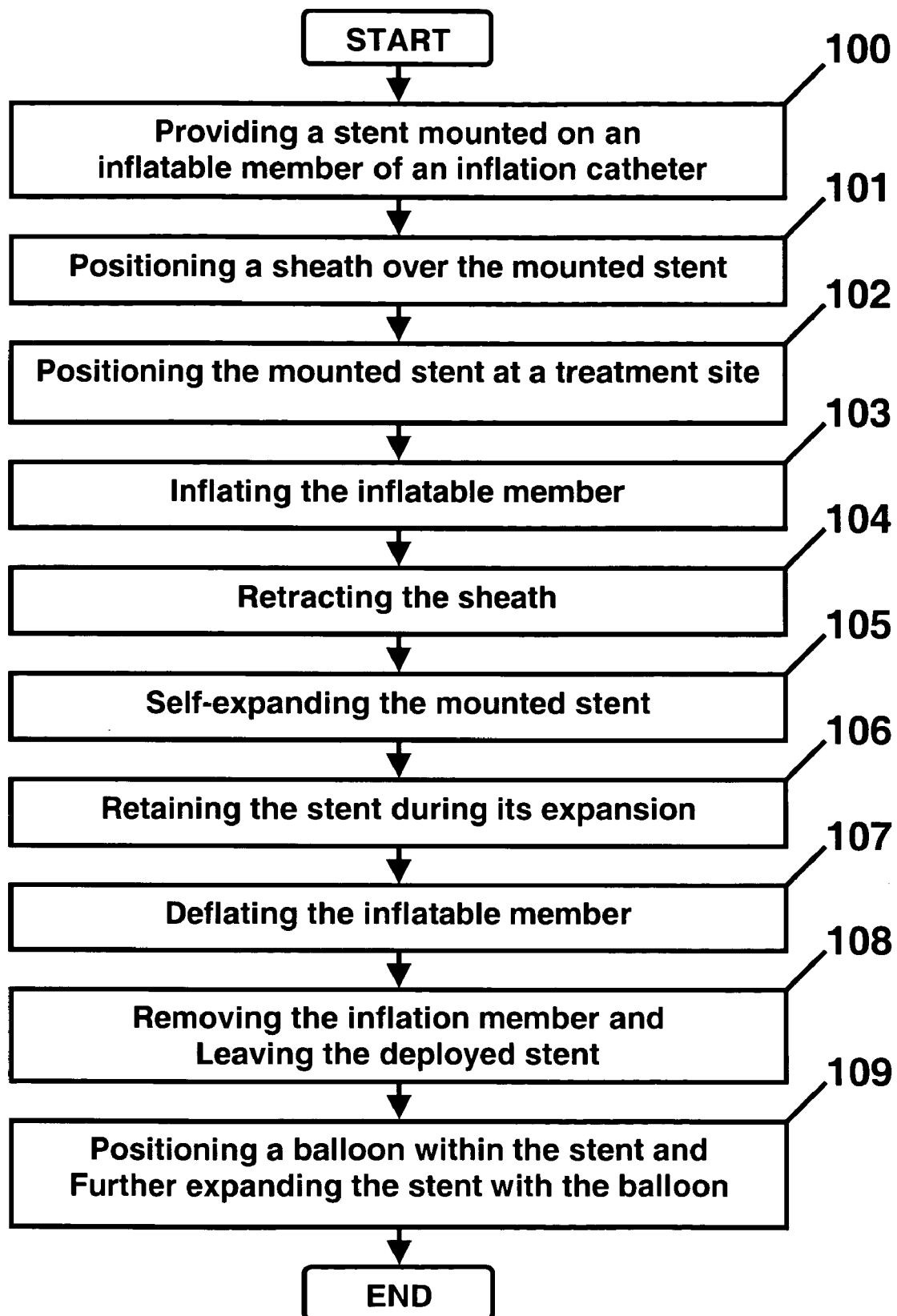
FIG. 1 is a flow chart of a method of deploying an intraluminal stent in a patient, in accordance with the present invention.

Referring to the drawings, wherein like reference numerals refer to like elements, FIG. 1 is a flow chart of one embodiment of a method of deploying an intraluminal stent in a patient, in accordance with the present invention. The following description relates primarily to the deployment of an intravascular, self-expanding stent following a balloon angioplasty procedure. Those skilled in the art will recognize that although the present invention is described primarily in the context of deploying a stent in a coronary artery with a specific intraluminal stent assembly, the inventor contemplates numerous other applications and variations to the stent assembly. For example, an intraluminal device according to the invention may be deployed within another blood vessel, arteriole or venous valve, intestine, air duct, esophagus, bile duct, and the like. Any number of devices capable of performing the prescribed function(s) may be adapted for use with the present invention. Furthermore, the deployment strategies and treatment site are not limited to those described. Numerous modifications, substitutions, additions, and variations may be made to the devices and methods while providing effective stent deployment consistent with the present invention.

Figure 2A:
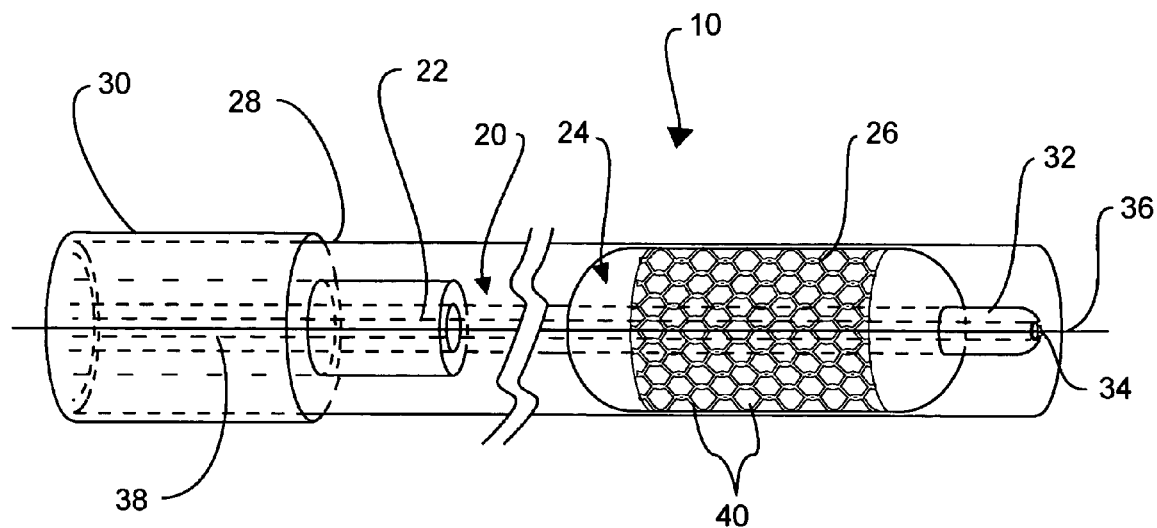
FIG. 2A is a schematic view of an intraluminal stent assembly in accordance with the present invention.

Stent deployment may begin by providing a self-expanding stent mounted on an inflatable member of an inflation catheter (step 100). In FIG. 2A, one embodiment of an intraluminal stent assembly in accordance with the present invention is shown generally by numeral 10. Assembly 10 comprises a catheter 20 including at least one lumen 22 formed therein. At least one inflatable member 24 is disposed on the catheter 20 and in communication with the lumen 22. The inflatable member 24 comprises at least one distal projection and at least one retention material, as discussed later. A self-expanding stent 26 is expandable from a compressed configuration to an expanded configuration. The stent 26 is disposed on the inflatable member 24 in the compressed configuration as shown.

In one embodiment of the present invention, the catheter 20 may comprise an elongated tubular member having substantially circular (in cross-section) inside and outside walls which are preferably substantially smooth. Catheter 20 may be secured at its proximal end to a suitable Luer fitting 30, and may include a distal rounded end 32 to reduce harmful contact with a vessel. Catheter 20 may be manufactured substantially from a material such as a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax®, Vestamid®, Tecoflex®, Halar®, Hyflon®, Pellathane®, combinations thereof, and the like. Catheter 20 may include an aperture 34 formed at the distal rounded end 32 allowing advancement over a guidewire 36. Catheter 20 may further include a drug delivery element for delivering therapeutic agents to the vessel. In one embodiment, the drug delivery element may include at least one elongated tube 38 positioned within the catheter 20. As such, the therapeutic agent(s) may be administered to the patient at an appropriate delivery site within the vessel.

Catheters typically comprise tubes made of one or more polymeric materials, sometimes in combination with metallic reinforcement. In some applications (such as smaller, more tortuous arteries), it is desirable to construct the catheter 20 from very flexible materials to facilitate advancement of catheters into such difficult access locations. Catheters are known in the art that provide different regions of flexibility (i.e., a stiffer proximal section and a more flexible distal section). Examples of such catheters include U.S. Pat. No. 4,464,176 issued to Wijayarathna, which describes a catheter made of two layers of tubing, one of the layers being more flexible than the other and extending distally beyond the end of the other layer by a considerable distance. U.S. Pat. No. 5,704,926 issued to Sutton describes a catheter that includes inner and outer tubular layers, and a continuous helical wire coil disposed between the tubular layers along substantially the entire length of the catheter. The wire coil is constructed to provide regions of differing flexibility to enhance catheter trackability and pushability.

In one embodiment, the stent 26 may be any variety of implantable prosthetic devices and may include a coating (including a therapeutic agent) as known in the art. Those skilled in the art will recognize that numerous stents, grafts, and implantable prosthetic devices are compatible with the disclosed deployment strategy and that the described stent 26 provides merely one example of the process. Stent 26 may include a generally tubular body defining a passageway extending along a longitudinal axis. Stent 26 may be formed from a plurality of cylindrical segments 40 arranged successively along its longitudinal axis.

Stent 26 is shown in a compressed state in which the cylindrical segments 40 have been compressed radially inward toward the longitudinal axis. Stent 26 may be compressed into a compact profile size for delivery within a vessel lumen at which time the stent 26 may be expanded to provide support to the vessel. Stent 26 is a self-expanding stent manufactured from one or more nickel titanium alloys and/or other alloys that exhibit superlastic behavior (i.e., capable of significant distortion without plastic deformation). Preferably, the stent 26 is manufactured from an inert, biocompatible material with high corrosion resistance.

In one embodiment, the inflatable member 24 comprises a balloon. Such balloons are known in the art for performing balloon type angioplasty, stent placement, and vessel repair/treatment procedures. The balloon may comprise a wide variety of inner structures, such as different lumen designs, including triple lumen, dual lumen and co-axial lumen. Most all varieties of internal structures and design variations are meant to be included herein. Inflatable member 24 may be manufactured substantially from a resilient material such as polyethylene, polyethylene terephthalate (PET), polyurethane, polyvinyl chloride, polyolefin, nylon, Pebax®, Pellathane®, Hytrel®; Artinel®, blends thereof, and the like. Inflatable member 24 includes at least one retention material for increasing the stent 26 retention during deployment. The at least one retention material may be coated onto the inflatable member 24 (i.e., by a dipping or spraying process) or integrated within the inflatable member 24 material itself. In one embodiment, inflatable member 24 has a relatively low-pressure inflation with an inflation pressure of about 0.05 to 1.50 ATM.

Figures 2B, 2C, 2D:
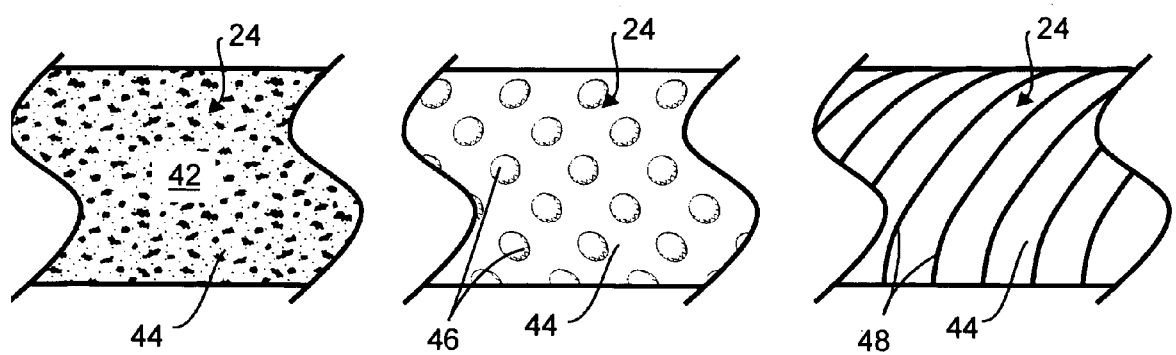
FIGS. 2B, 2C, and 2D are alternative embodiment detailed schematic views of an inflatable member outer layer of the assembly of FIG. 2A, in accordance with the present invention.

As shown in FIG. 2B, the inflatable member 24 may include at least one retention material such as adhesive 42 disposed on its outer layer 44. Numerous adhesives and other coatings are known in the art for increasing stent retention on the inflatable member 24 (i.e., by increasing tackiness) and for other beneficial effects. Such substances may be adapted for use with the present invention. In addition to or in lieu of the outer layer 44 adhesives/coatings, the at least one retention material may comprise at least one surface feature on the inflatable member 24. The surface feature may comprise a plurality of bumps 46 as shown in FIG. 2C, a plurality of ridges 48 as shown in FIG. 2C, and/or any variety of textured surfaces. The surface feature may comprise any number and type of surface geometries for increasing frictional retention of the stent. Those skilled in the art will recognize that the arrangement, variety, and combination of the inflatable member 24 adhesive(s), coating(s), and surface feature(s) may be varied while providing effective stent retention and deployment in accordance with the present invention.

A sheath 28 is positioned over the mounted stent 26 (step 101). In one embodiment, the sheath 28 may be slid over the stent 26 as known in the art. Sheath 28 may comprise an elongated tubular member having substantially circular (in cross-section) inside and outside walls which are preferably substantially smooth. Sheath 28 may retain the self-expanding stent 26, which would otherwise expand, in the compressed configuration on the inflatable member 24. In addition, the sheath 28 may provide an even outer surface on the assembly 10 for negotiation through narrowed vessels.

Figure 3:
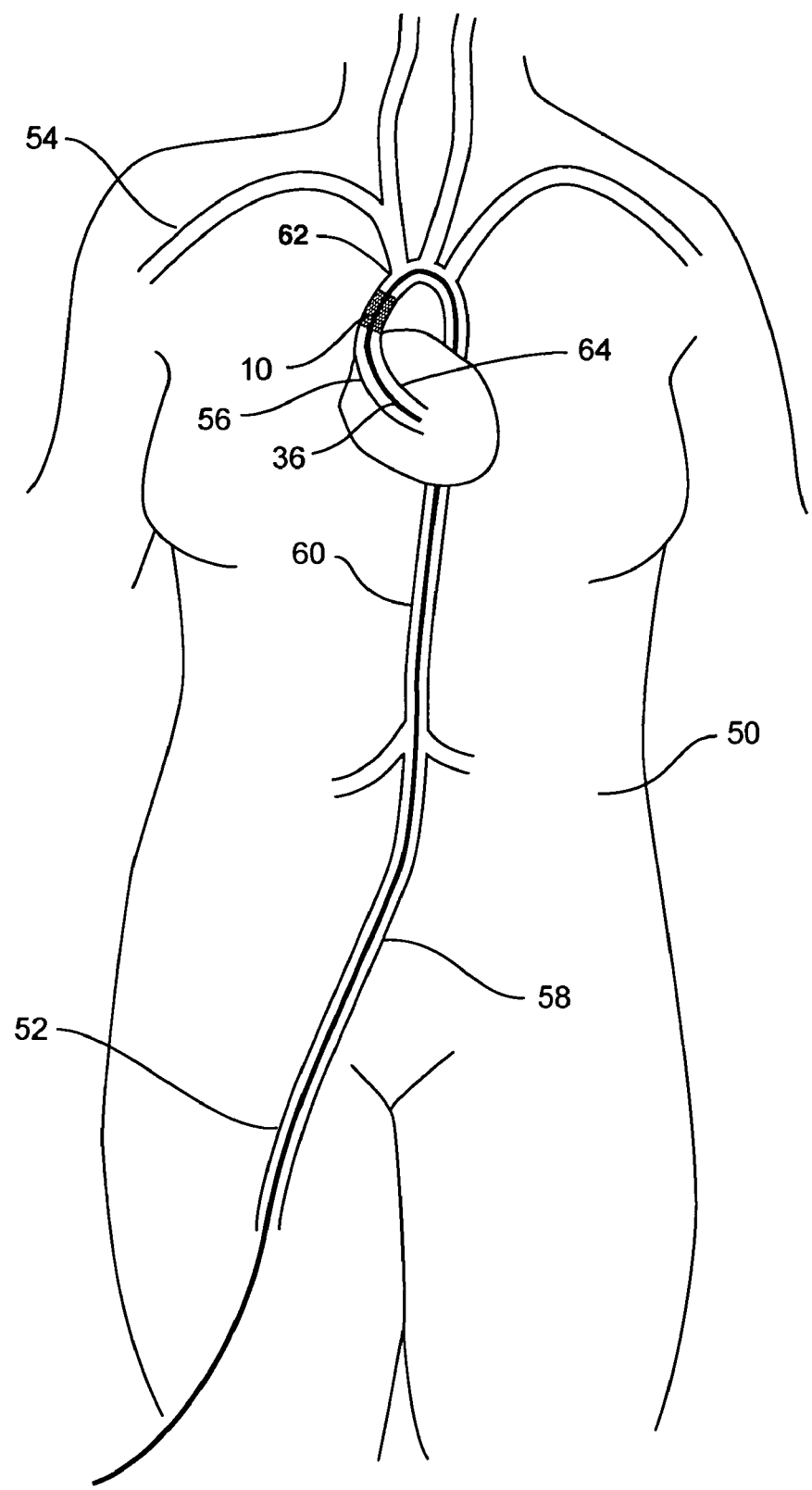
FIG. 3 is a schematic view of a patient undergoing an intraluminal stent assembly deployment procedure in accordance with the present invention.

As shown in FIG. 3, the assembly 10 may be inserted into a blood vessel lumen, such as through an incision made in a patient 50 femoral artery 52 (as shown), a brachial artery 54, or another vessel as understood in the art. Assembly 10 may be advanced along the pre-positioned flexible guidewire 36 to access a treatment site 56 through a vessel pathway, which in this case includes an iliac artery 58 and abdominal aorta 60. Assembly 10 may then be advanced through an aortic arch 62 to descend into the aortic cusp where entry is gained to a coronary artery blood vessel 64 and the treatment site 56. It is important to note that vessel pathways other than those described may be used with the present invention to access a given treatment site.

Figure 4A:
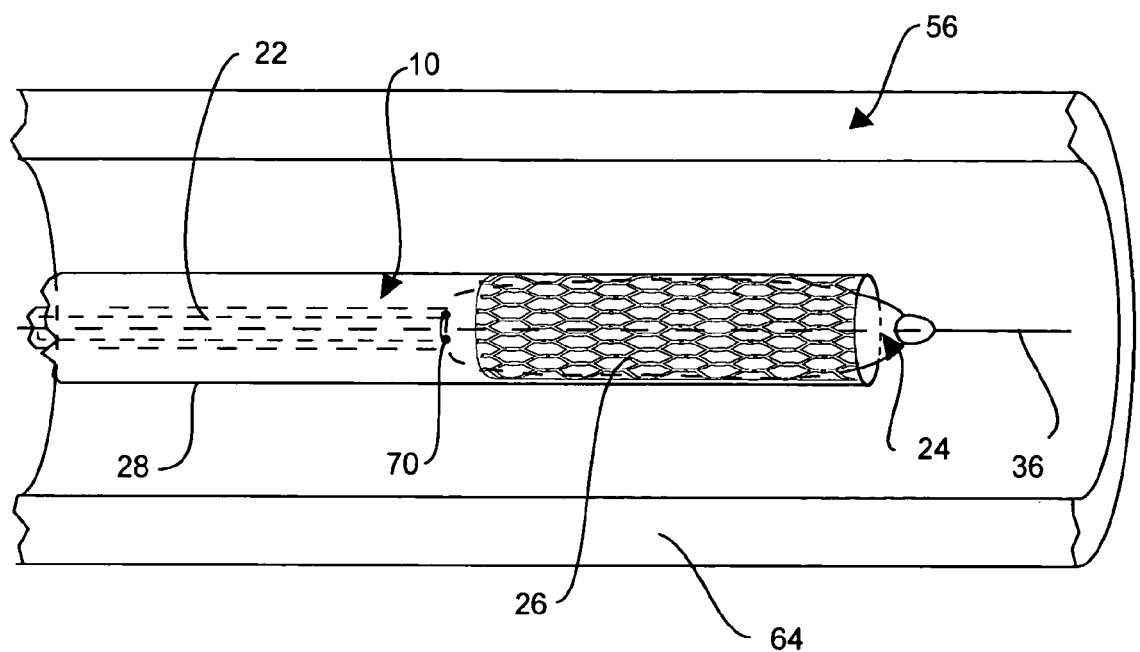
FIGS. 4A, 4B, 4C, 4D, 4E, and 4F are sequential detailed schematic views of an intraluminal stent assembly deployment procedure in accordance with the present invention.

Stent 26 may then be positioned at the treatment site 56 within a body lumen (step 102), which in this case is the coronary artery blood vessel 64. The positioning of the stent 26 and its subsequent deployment are illustrated in FIGS. 4A through 4F. The positioning of the stent 26 may be determined by visualization methods known in the art, such as fluoroscopy and/or intravascular ultrasound (IVUS). Assembly 10 may include one or more radiopaque markers 70 to enhance the positioning process. The radiopaque material may comprise barium sulfate, gold, silver, tantalum oxide, tantalum, platinum, platinum/iridium alloy, tungsten, and other materials typically used to assist intravascular device positioning. As shown in FIG. 4A, the stent 26 may be positioned at the treatment site 56, which, for example, may have been previously treated with PTCA. As such, the stent 26 may prevent restenosis of the blood vessel 64.

Figure 4B:
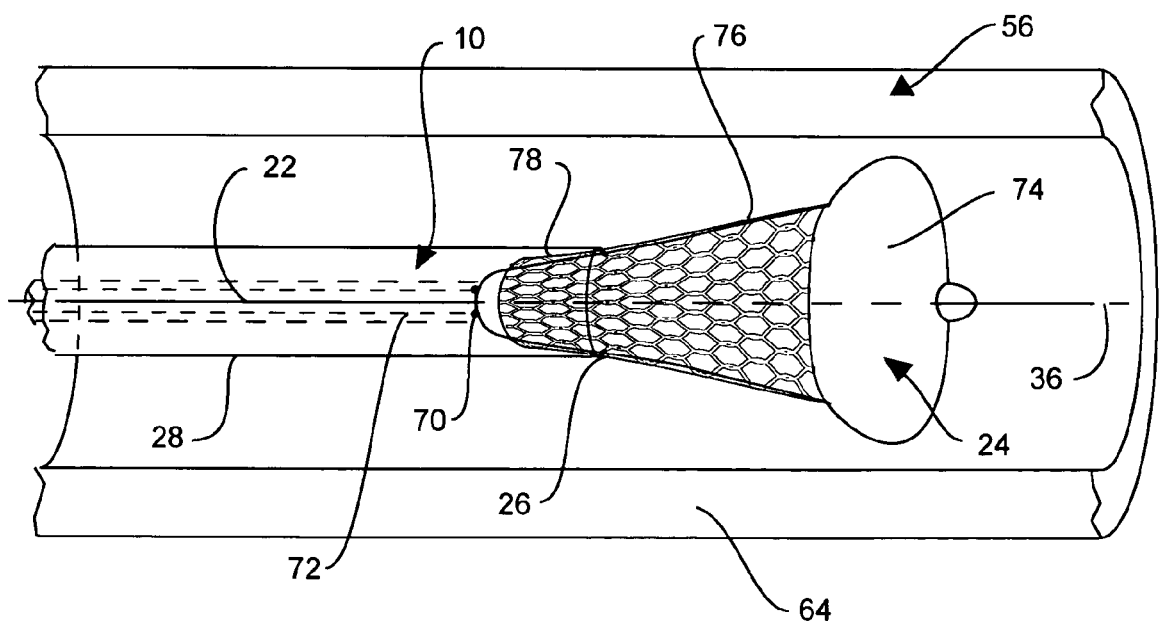
Figure 4C:
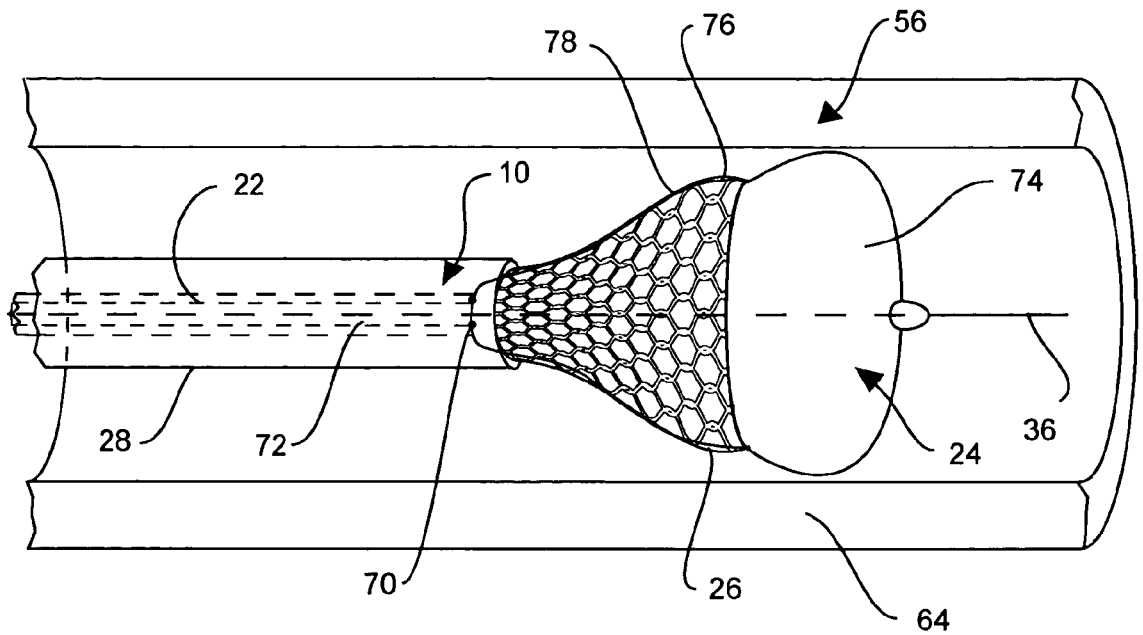

Referring to FIGS. 4B and 4C, the inflatable member 24 is inflated (step 103). Inflatable member 24 may be inflated prior to insertion of the assembly 10 within the patient or, alternatively, just before deployment of the stent 26. The inflation may be achieved by flowing a fluid 72, such as a radiopaque contrast liquid, into the interior of the inflatable member 24 through the lumen 22. In one embodiment, the inflation rate is maintained. As the inflation begins, the distal portion of the inflatable member 24 may first project radially outward forming a distal projection such as a "pillow" structure 74. Structure 74, along with the retention material, reduces stent 26 slippage during deployment. In one embodiment, the structure 74 is a distal pillow member. Those skilled in the art will appreciate that the inflatable member 24 distal projection may comprise any number and variety of projection geometries other than the "pillow" structure 74. For example, the distal projection may include several finger like projections adapted for reducing stent 26 slippage during deployment. In another embodiment, the stent is retained during expansion with at least one retention material. The at least one retention material may adhesively retain the stent, frictionally retain the stent, or both.

In one embodiment, the inflatable member 24 may be inflated with a relatively low inflation pressure of about 0.05 to 1.50 ATM. As the inflatable member 24 expands, the inflation rate may be maintained to keep up with the increase in balloon volume. The maintenance of the inflatable member 24 inflation rate may be achieved with one or more operators and/or a device, such as an indeflator device adapted for such a purpose, as known in the art.

Figure 4D:
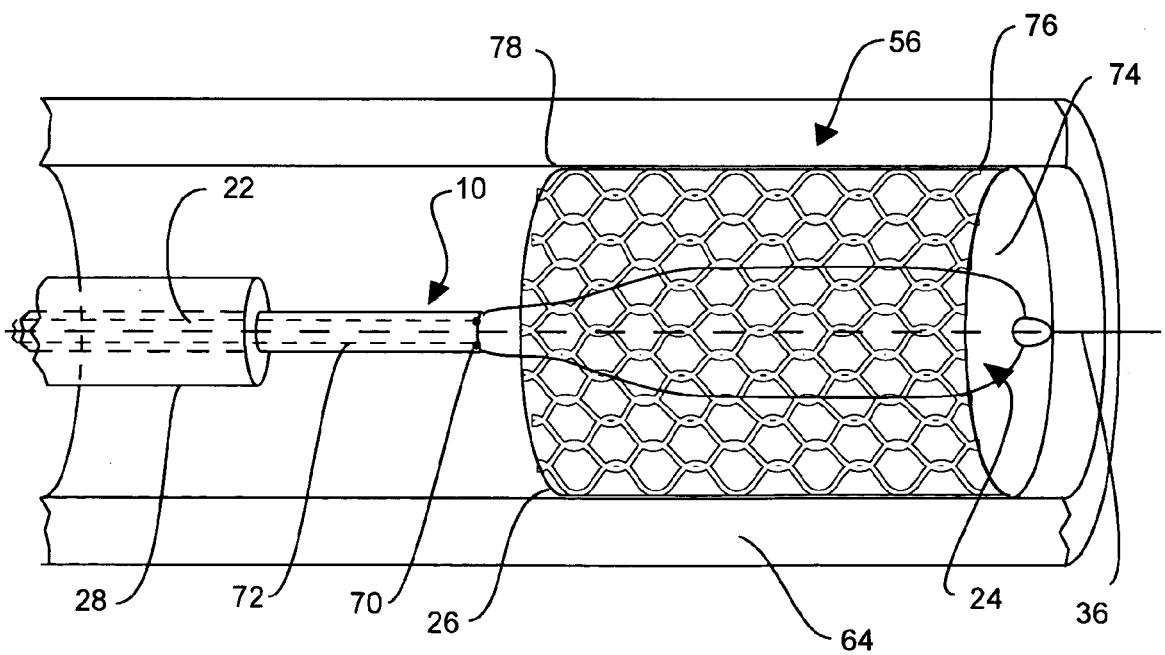

Referring to FIGS. 4B through 4D, the sheath 28 is retracted (step 104) and the stent 26 self-expands (step 105). In one embodiment, the self-expanding stent 26 naturally assumes its expanded configuration upon retraction of the sheath 28. As shown, the stent 26 may expand progressively as the sheath is retracted wherein the stent 24 distal portion 76 expands before its proximal portion 78. Sheath 28 may be retracted manually by an operator and/or a device known in the art and adapted for such a purpose, as known in the art. Stent 26 is retained during its expansion with the distal projection(s) (e.g., the distal pillow structure 74; step 106), and with the retention material(s) (e.g., adhesive retention and/or frictional retention). As previously described, retaining the stent 26 in this manner may limit jumping and slippage thereby increasing the accuracy of stent 26 placement.

Figure 4E:
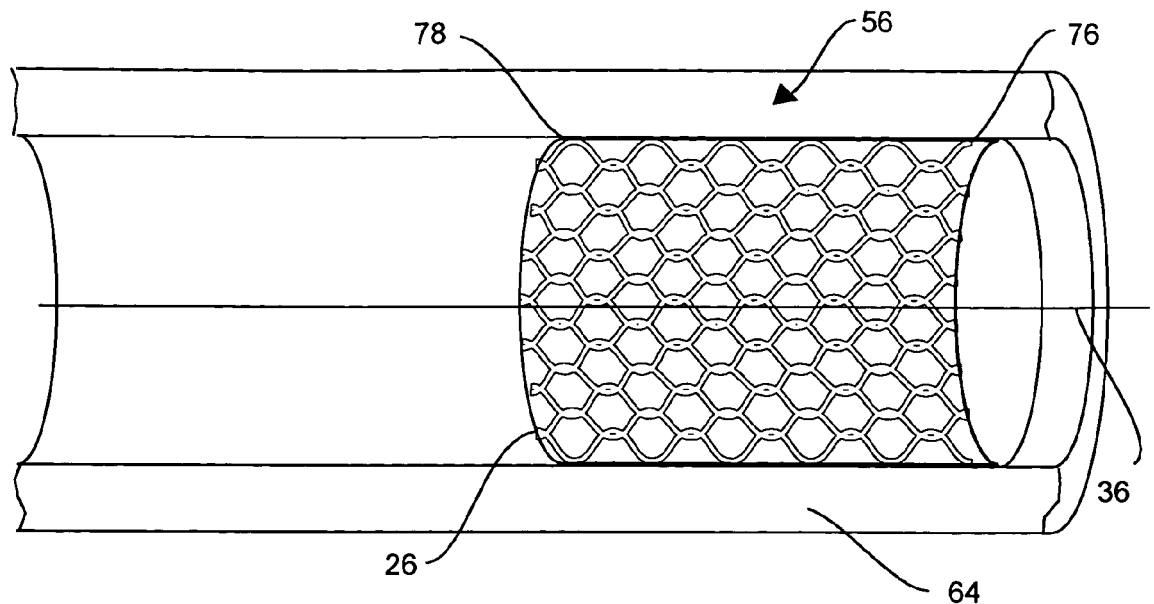
Figure 4F:
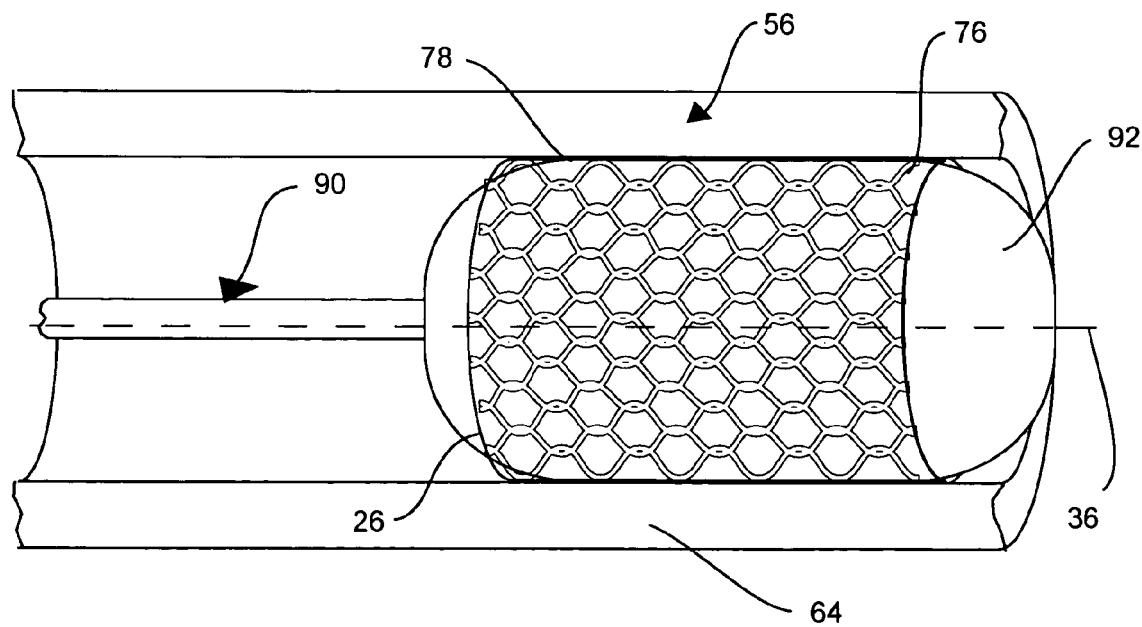

After stent 26 deployment, the inflatable member 24 is deflated (step 107) as shown in FIG. 4D. Deflation may be achieved by slowly withdrawing the fluid 72 from the inflatable member 24. Assembly 10 including the inflatable member 24 is then withdrawn from the patient (step 108) leaving the deployed stent 26 as shown in FIG. 4E. In some cases, it may be desirable to further expand the deployed stent 26 to ensure complete deployment. To achieve this, the guidewire 36 is typically left in place while the rest of the assembly 10 is removed from the patient. A catheter exchange may be performed wherein another catheter 90 including a balloon 92 may be positioned within the deployed stent 26 (step 109), as shown in FIG. 4F. Once positioned, the balloon 92 may be inflated beyond the diameter of the deployed stent 26 ensuring that the stent 26 is completely expanded. The balloon 92 may then be deflated and the catheter 90 and guidewire 36 removed from the patient to complete the intraluminal stent deployment procedure.

While the embodiments of the invention disclosed herein are presently considered to be preferred, various changes and modifications may be made without departing from the spirit and scope of the invention. The intraluminal stent assembly and deployment strategy of the present invention are not limited to any particular design, configuration, methodology, or sequence. For example, the catheter, inflatable member, stent, sheath, guidewire, and treatment site may vary without limiting the utility of the invention. Furthermore, the described order may vary and may include additional steps to provide effective stent deployment Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

The invention claimed is:

1. An intraluminal stent assembly comprising:
   a catheter including at least one lumen formed therein;
   at least one inflatable member disposed on the catheter and in communication with the lumen, the inflatable member comprising at least one distal projection, the distal projection having a first expansion diameter;
   a self-expanding stent expandable from a compressed configuration to an expanded configuration, the stent having a second expansion diameter, the stent disposed on the inflatable member in the compressed configuration, the stent disposed on the inflatable member proximal to the at least one distal projection; and
   a sheath slidably positioned over the stent wherein the stent expands itself to the expanded configuration upon retraction of the sheath;
   wherein the inflatable member is inflatable with a fluid flowing through the lumen-such that the distal projection expands in diameter more rapidly than the stent self-expands, wherein the first expansion diameter is greater than the second expansion diameter to retain the stent on the inflatable member while the stent self-expands during deployment.

2. The assembly of claim 1 wherein the inflatable member comprises a balloon.

3. The assembly of claim 1 wherein the distal projection projects radially outward when the inflatable member is inflated.

4. The assembly of claim 1 wherein the distal projection comprises a distal pillow member.

5. The assembly of claim 1 further comprising a balloon positioned within the expanded stent to further expand the stent.

6. A method of deploying an intraluminal stent, the method comprising:
   providing a self-expanding stent mounted on at least one inflatable member of an inflation catheter, the inflatable member comprising at least one distal projection, the distal projection having a first expansion diameter and the stent having a second expansion diameter;
   positioning a sheath over the mounted stent;
   positioning the mounted stent at a treatment site within a body lumen;
   inflating the inflatable member;

expanding the at least one distal projection to the first expansion diameter distal to a distal end of the stent;

retracting the sheath to self-expand the stent to the second expansion diameter;

retaining the stent during self-expansion with the distal projection wherein the first expansion diameter is greater than the second expansion diameter;

deflating the inflatable member; and removing the inflation catheter from the body lumen whereby the expanded stent remains deployed at the treatment site in the body lumen.

7. The method of claim 6 wherein the inflatable member comprises a balloon.

8. The method of claim 6 wherein inflating the inflatable member comprises projecting the distal projection radially outward.

9. The method of claim 6 wherein inflating the inflatable member comprises maintaining an inflation rate wherein the first expansion diameter is greater than the second expansion diameter.

10. The method of claim 6 further comprising:
positioning a compressed balloon within the deployed stent; and
expanding the balloon to further expand the deployed stent.

11. An intraluminal stent assembly comprising:
a catheter including at least one lumen formed therein;
at least one inflatable member disposed on the catheter and in communication with the lumen, the inflatable member comprising at least one retention material;
a self-expanding stent expandable from a compressed configuration to an expanded configuration, the stent disposed on the inflatable member in the compressed configuration; and
a sheath slidably positioned over the stent wherein the stent expands itself to the expanded configuration upon retraction of the sheath;
wherein the inflatable member is inflatable with a fluid flowing through the lumen-such that the at least one retention material retains the stent on the inflatable member while the stent expands itself.

12. The assembly of claim 11 wherein the inflatable member comprises a balloon.

13. The assembly of claim 11 wherein the at least one retention material comprises at least one material selected from a group consisting of at least one adhesive and at least one surface feature.

14. The assembly of claim 13 wherein the at least one surface feature comprises at least one feature selected from a group consisting of bumps, ridges, and textures.

15. The assembly of claim 11 further comprising a balloon positioned within the expanded stent to further expand the stent.

16. A method of deploying an intraluminal stent, the method comprising:
providing a self expanding stent mounted on at least one inflatable member of an inflation catheter, the inflatable member comprising at least one retention material;
positioning a sheath over the mounted stent;
positioning the mounted stent at a treatment site within a body lumen;
inflating the inflatable member;
retracting the sheath to self-expand the stent;
retaining the stent during its expansion with the at least one retention material;
deflating the inflatable member; and
removing the inflation catheter from the body lumen whereby the stent remains deployed at the treatment site in the body lumen.

17. The method of claim 16 wherein the inflatable member comprises a balloon.

18. The method of claim 16 wherein inflating the inflatable member comprises maintaining an inflation rate.

19. The method of claim 16 wherein retaining the stent during its expansion with the at least one retention material comprises adhesively retaining the stent.

20. The method of claim 16 wherein retaining the stent during its expansion with the at least one retention material comprises frictionally retaining the stent.

21. The method of claim 16 further comprising:
positioning a compressed balloon within the deployed stent; and
expanding the compressed balloon to further expand the deployed stent.

* * * * *

UNITED STATES PATENT AND TRADEMARK OFFICE
CERTIFICATE OF CORRECTION

PATENT NO. : 7,651,525 B2
APPLICATION NO. : 10/911931
DATED : January 26, 2010
INVENTOR(S) : Mark J. Dolan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1225 days.

Signed and Sealed this

Twenty-third Day of November, 2010

David J. Kappos
*Director of the United States Patent and Trademark Office*